United States Patent [19]

Oxford et al.

[11] Patent Number: 5,001,135
[45] Date of Patent: Mar. 19, 1991

[54] INDOLE DERIVATIVES

[75] Inventors: Alexander W. Oxford; Peter C. North; Martin R. Johnson, all of Ware, England

[73] Assignee: Glaxo Group Limited, London, England

[21] Appl. No.: 477,466

[22] Filed: Feb. 9, 1990

[30] Foreign Application Priority Data

Feb. 10, 1989 [GB] United Kingdom ............... 8903036

[51] Int. Cl.$^5$ ................. A61K 31/445; C07D 401/04
[52] U.S. Cl. .................................... 514/323; 546/201
[58] Field of Search .................. 546/201; 514/323

[56] References Cited

U.S. PATENT DOCUMENTS

| | | | |
|---|---|---|---|
| 2,183,235 | 5/1965 | Zenitz | 546/201 |
| 3,217,811 | 11/1965 | Zenitz | 546/201 |
| 3,238,215 | 3/1966 | Zenitz | 546/201 |
| 3,409,626 | 11/1968 | Cavallko | 546/201 |

FOREIGN PATENT DOCUMENTS

36833/68 4/1968 Australia .
1410783 10/1975 United Kingdom .

Primary Examiner—Mary C. Lee
Assistant Examiner—Peter James Davis
Attorney, Agent, or Firm—Bacon & Thomas

[57] ABSTRACT

Compounds are disclosed of formula (I)

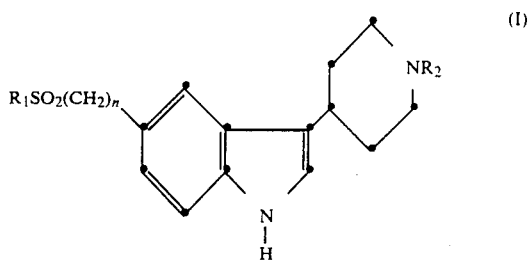

wherein
$R_1$ represents a $C_{1-6}$alkyl group;
$R_2$ represents a hydrogen atom or a $C_{1-3}$alkyl group;
n represents zero or an integer from 1 to 3;
and pharmaceutically acceptable salts thereof.

The compounds are useful for the treatment of migraine, cluster headache, chronic paroxysmal hemicrania and headache associated with vascular disorders.

Processes and intermediates for their preparation and pharmaceutical compositions containing them are also disclosed.

13 Claims, No Drawings

INDOLE DERIVATIVES

This invention relates to indole derivatives, to processes for their preparation, to pharmaceutical compositions containing them and to their medical use, in particular to compounds and compositions of use in the treatment of migraine.

It has been suggested that the pain of migraine may be associated with excessive dilatation of the cranial vasculature and known treatments for migraine include the administration of compounds having vasoconstrictor properties such as ergotamine. However, ergotamine is a non-selective vasoconstrictor which constricts blood vessels throughout the body and has undesirable and potentially dangerous side effects. Migraine may also be treated by administering an analgesic usually in combination with an antiemetic but such treatments are of limited value.

More recently, indole derivatives which are selective $5HT_1$-like receptor agonists and which exhibit selective vasoconstrictor activity have been described in the art as useful in the treatment of migraine.

We have now found a novel group of indole derivatives which exhibit $5HT_1$-like receptor agonist activity and selective vasoconstriction.

Thus, the present invention provides a compound of formula (I):

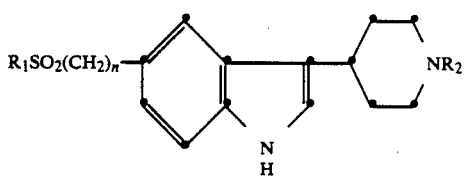

wherein $R_1$ represents a $C_{1-6}$alkyl group;
$R_2$ represents a hydrogen atom or a $C_{1-3}$ alkyl group;
n represents zero or an integer from 1 to 3;
and pharmaceutically acceptable salts thereof.

As used herein an alkyl group may be a straight or branched chain alkyl group, for example a methyl, ethyl or isopropyl group. A $C_{1-6}$ alkyl group is conveniently a $C_{1-3}$ alkyl group such as methyl or ethyl.

In one preferred class of compounds of formula (I) $R_1$ represents a $C_{1-3}$alkyl group for example methyl.

$R_2$ may be, for example, a hydrogen atom but is preferably a methyl group.

In one preferred class of compounds of formula (I) n represents 2.

An alternative preferred class of compounds falling within the scope of formula (I) has the formula (Ia)

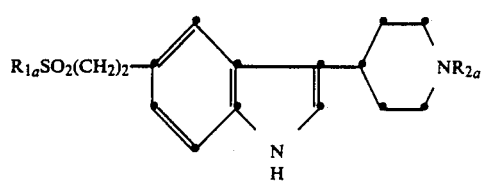

wherein $R_{1a}$ represents a $C_{1-6}$ (preferably $C_{1-3}$) alkyl group such as methyl; and $R_{2a}$ represents a hydrogen atom or a $C_{1-3}$alkyl group such as methyl;
and pharmaceutically acceptable salts thereof.

A preferred compound according to the invention is 3-(1-methyl-4-piperidinyl)-5-[2-(methylsulphonyl)ethyl]-1H-indole and its pharmaceutically acceptable salts.

Suitable pharmaceutically acceptable salts are those conventionally known in the art. Examples of pharmaceutically acceptable salts include acid addition salts formed with inorganic acids, such as hydrochlorides, hydrobromides, phosphates and sulphates, and with organic acids, for example tartrates, maleates, fumarates, succinates and sulphonates. Other salts which are not pharmaceutically acceptable may be useful in the preparation of compounds of formula (I) and these form a further part of the invention.

Compounds of the invention may readily be isolated in association with solvent molecules by crystallisation from or evaporation of an appropriate solvent. It is intended to include such solvates within the scope of the present invention.

The selective $5HT_1$-like receptor agonist activity and selective vasoconstrictor activity of the compounds of the invention have been demonstrated in vitro. In addition, compounds of the invention selectively constrict the carotid arterial bed of the anaesthetised dog whilst having negligible effect on blood pressure.

Compounds of the invention are useful in treating conditions associated with cephalic pain. In particular the compounds are useful in the treatment of migraine, cluster headache, chronic paroxysmal hemicrania and headache associated with vascular disorders and in alleviating the symptoms associated therewith.

Accordingly, the invention also provides a pharmaceutical composition which comprises at least one compound of formula (I) or a pharmaceutically acceptable salt thereof and formulated for administration by any convenient route. Such compositions are preferably in a form adapted for use in medicine, in particular human medicine, and can conveniently be formulated in conventional manner using one or more pharmaceutically acceptable carriers or excipients.

In a further aspect there is provided a compound of formula (I) or a pharmaceutically acceptable salt or solvate thereof for use in therapy, in particular in human medicine. It will be appreciated that use in therapy embraces but is not necessarily limited to use of a compound of formula (I) or a pharmaceutically acceptable salt thereof as an active therapeutic substance.

There is also provided as a further aspect of the invention the use of a compound of formula (I) in the preparation of a medicament for use in the treatment of conditions associated with cephalic pain in particular migraine, cluster headache, chronic paroxysmal hemicrania and headache associated with vascular disorders.

In an alternative or further aspect there is provided a method for the treatment of a mammal, including man, comprising administration of an effective amount of a compound of formula (I) or a pharmaceutically acceptable salt thereof in particular in the treatment of conditions associated with cephalic pain and in alleviating the symptoms associated therewith.

It will be appreciated that reference to treatment is intended to include prophylaxis as well as the alleviation of established symptoms. Compounds according to the invention may be administered as the raw chemical but the active ingredient is preferably presented as a pharmaceutical formulation.

The active ingredient may conveniently be presented in unit dose form. A convenient unit dose formulation contains the active ingredient compound in an amount of from 0.1 mg to 250 mg.

The compounds according to the invention may for example be formulated for oral, sub-lingual, buccal, parenteral, rectal or intranasal administration or in a form suitable for administration by inhalation or insufflation (either through the mouth or nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl-p-hydroxybenzoates or sorbic acid).

For buccal administration the compositions may take the form of tablets or lozenges formulated in conventional manner.

The compounds of the invention may be formulated for parenteral administration by injection, conveniently intravenous or subcutaneous injection, for example by bolus injection or continuous intravenous infusion. Formulations for injection may be presented in unit dosage form e.g. in ampoules or in multi-dose containers, with an added preservative.

The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of the invention may also be formulated in rectal compositions such as suppositories or retention enemas, e.g. containing conventional suppository bases such as cocoa butter or other glyceride.

Tablets for sub-lingual administration may be formulated in a similar manner to those for oral administration.

For intranasal administration the compounds of the invention may be used, for example, as a liquid spray or powder or in the form of drops.

For administration by inhalation the compounds according to the invention are conveniently delivered in the form of an aerosol spray presentation from pressurised packs or a nebuliser, with the use of a suitable propellant, e.g. dichlorodifluoromethane, trichlorofluoromethane, dichlorotetrafluoroethane, carbon dioxide or other suitable gas. In the case of a pressurised aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

It will be appreciated that the precise dose administered will depend on the age and condition of the patient, the particular compound used and the frequency and route of administration. The compound may be administered in single or divided doses and may be administered one or more times, for example 1 to 4 times per day.

A proposed dose of the compounds of the invention for oral, sublingual, parenteral, buccal, rectal or intranasal administration to man (of approximately 70 kg bodyweight) for the treatment of migraine is 0.1 to 250 mg of the active ingredient per unit dose which could be administered, for example, 1 to 4 times per day.

For oral administration a unit dose will preferably contain from 2 to 200 mg for example 100 mg of the active ingredient. A unit dose for parenteral administration will preferably contain 0.2 to 25 mg of the active ingredient.

Aerosol formulations are preferably arranged so that each metered dose or 'puff' delivered from a pressurised aerosol contains 0.2 mg to 2 mg of a compound of the invention, and capsules and cartridges delivered from an insufflator or an inhaler, contain 0.2 mg to 20 mg of a compound of the invention. The overall daily dose by inhalation with an aerosol will be within the range 1 mg to 250 mg. Administration may be several times daily, for example from 2 to 8 times, giving for example 1, 2 or 3 doses each time.

Dosages of the compounds of the invention for rectal and sub-lingual administration are similar to those for oral administration. For intranasal administration a unit dose will preferably contain from 10 to 100 mg of the active ingredient.

The compounds of the invention may, if desired, be administered in combination with one or more other therapeutic agents, such as analgesics, anti-inflammatory agents and anti-nauseants, and formulated for administration by any convenient route in conventional manner. Appropriate doses will be readily appreciated by those skilled in the art.

Compounds of formula (I) may be prepared by the methods outlined below and which form a further aspect of the invention. In the following processes $R_1$, $R_2$ and n are as defined for formula (I) unless otherwise specified.

According to one general process (A), a compound of formula (I) may be prepared by cyclisation of a compound of formula (II)

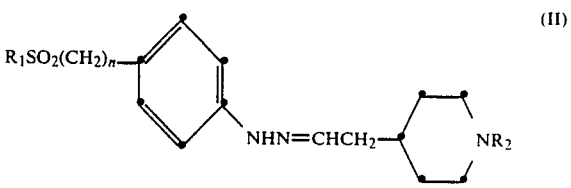

The process is desirably carried out in the presence of polyphosphate ester in a reaction medium which may comprise one or more organic solvents, preferably halogenated hydrocarbons such as chloroform, dichloromethane, dichloroethane, dichlorodifluoromethane, or mixtures thereof. Polyphosphate ester is a mixture of esters which may be prepared from phosphorus pentoxide, diethylether and chloroform according to the method described in 'Reagents for Organic Synthesis', (Fieser and Fieser, John Wiley and Sons 1967).

Alternatively the cyclisation may be carried out in aqueous or non-aqueous media, in the presence of an acid catalyst. When an aqueous medium is employed this may be an aqueous organic solvent such as an aqueous alcohol (e.g. methanol, ethanol or isopropanol) or an aqueous ether (e.g. dioxan or tetrahydrofuran) as well as mixtures of such solvents and the acid catalyst may be for example an inorganic acid such as concentrated hydrochloric, sulphuric or polyphosphoric acid. (In some cases the acid catalyst may also act as the reaction solvent). In an anhydrous reaction medium, which may comprise one or more alcohols or ethers (e.g. as described above) or esters (e.g. ethyl acetate), the acid catalyst will generally be a Lewis acid such as boron trifluoride, zinc chloride or magnesium chloride. The cyclisation reaction may conveniently be carried out at temperatures of from 20° to 200° C. preferably 50° to 125° C.

According to a particular embodiment of this process, compounds of formula (I) may be prepared directly by the reaction of a compound of formula (III):

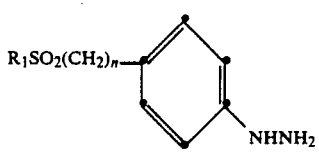

or a salt thereof, with a compound of formula (IV)

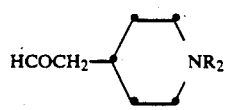

or a salt or protected derivative thereof (such as an acetal formed, for example, with an appropriate alkylorthoformate) using the appropriate conditions as described above. It will be appreciated that in this embodiment, a compound of formula (II) is formed as an intermediate, and may be reacted in situ to form the desired compound of general formula (I).

Compounds of general formula (II) may, if desired, be isolated as intermediates during the process for the preparation of compounds of formula (I) wherein a compound of formula (III), or a salt or protected derivative thereof, is reacted with a compound of formula (IV), or a salt or protected derivative thereof, in water or in a suitable solvent, such as an aqueous alcohol (e.g. methanol) at a temperature of, for example, 20° to 100° C. If an acetal or ketal of a compound of formula (IV) is used, it may be necessary to carry out the reaction in the presence of an acid (for example, acetic or hydrochloric acid).

Compounds of general formula (III) may be prepared in a number of conventional steps, from compounds of formula (V):

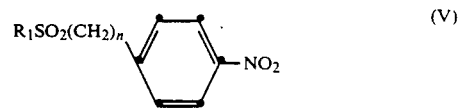

For example, a compound of formula (V) may be reduced by catalytic hydrogenation using a catalyst such as palladium on charcoal to give an amine which may be diazotised using, for example nitrous acid and the product of this reaction may then be reduced using, for example, stannous chloride to give a compound of formula (III).

According to another general process (B), a compound of formula (I) wherein n is 2 or 3 may be prepared by reduction of a compound of formula (VI)

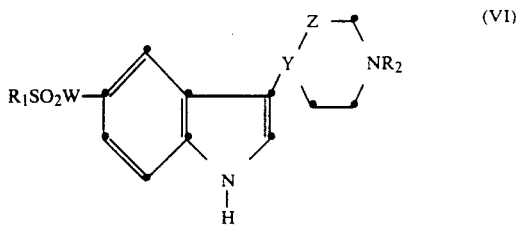

(wherein W represents the group $(CH_2)_n$ or a $C_{2-3}$alkenyl moiety, QCH=CH wherein Q is a bond or a methylene group; and Y-Z represents $CH—CH_2$ or C=CH).

The reduction process may conveniently be carried out in the presence of hydrogen and a noble metal catalyst, such as palladium, Raney nickel, platinum, platinum oxide or rhodium which may be supported, for example, on charcoal. Alternatively a homogeneous catalyst such as tris(triphenylphosphine) rhodium chloride may be used.

General process (B) may be effected in the presence of solvent. An anhydrous or aqueous reaction medium comprising one or more solvents may be employed. Suitable solvents include alcohols, for example methanol or ethanol, amides, for example dimethylformamide, ethers for example dioxan or esters for example ethylacetate. The reaction may conveniently be carried out at a temperature of from $-10°$ to $+50°$ C., preferably about 25° C.

Compounds of formula (VI) are novel and form a further feature of the invention.

Compounds of formula (VI) wherein W represents a group QCH=CH may be prepared by reacting a compound of formula (VII)

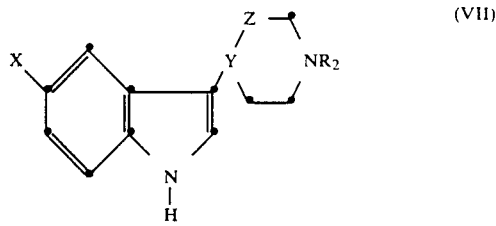

(wherein X represents a leaving atom or group such as a halogen atom for example a bromine atom) with an alkene $R_1SO_2QCH=CH_2$.

The reaction will generally be effected in the presence of a palladium catalyst and a base. The catalyst may be, for example, palladium on charcoal or a palladium salt. Palladium salts which may be employed as catalysts include salts of organic acids such as acetates or salts of inorganic acids such as chlorides or bromides. The base may be, for example, a tertiary nitrogen base such as triethylamine or tri-n-butylamine or an alkali metal carbonate such as sodium carbonate. The reaction may optionally be carried out in the presence of a phosphine, for example a triarylphosphine such as triphenylphosphine or tri-o-tolylphosphine. A phosphine should be present when the process is effected with a compound of formula (VII) wherein X represents a bromine atom.

Compounds of formula (VII) are either known compounds or may be prepared from known compounds by methods analogous to those described herein.

Compounds of formula (VI) wherein Y-Z represents C=CH may be prepared by condensing a compound of formula (VIII):

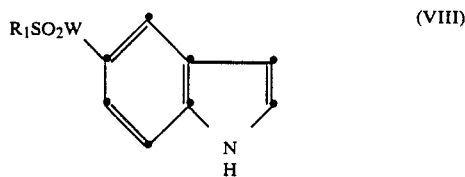

or a protected or activated derivative thereof, with a piperidine of formula (IX):

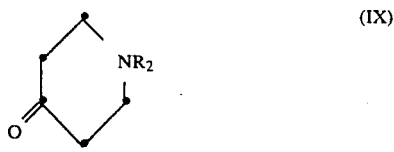

or a salt or protected derivative thereof.

The condensation reaction may be effected in a suitable reaction medium in the presence of an acid or a base, conveniently at a temperature of 25° to 120° C.

Acids which may be employed in the above process include organic and inorganic acids such as sulphonic acids (e.g. p-toluenesulphonic acid), carboxylic acids (e.g. acetic acid) and preferably strong inorganic acids such as polyphosphoric acid, sulphuric acid and hydrochloric acid. Suitable solvents for the reaction include inert solvents such as ethers (e.g. tetrahydrofuran or dioxan), alcohols (e.g. ethanol) and chlorinated hydrocarbons (e.g. chloroform or carbon tetrachloride). In some cases the acid may also act as the reaction solvent.

Bases which may be employed in the above process include alkali metal hydroxides (e.g. potassium hydroxide), alkali metal alkoxides (e.g. sodium or potassium methoxide, ethoxide or t- butoxide), alkali metal hydrides (e.g. sodium hydride) and alkali metal amides (e.g. sodamide). Suitable solvents for the reaction include alcohols (e.g. methanol or ethanol), ethers (e.g. tetrahydrofuran or dioxan) and dimethylsulphoxide.

Intermediates of formula (VIII) wherein W represents a group QCH=CH may be prepared by condensation of a 3-unsubstituted analogue of (VII) with an alkene $R_1SO_2QCH=CH_2$ as described above.

Intermediates of formula (VIII) wherein W represents a group $(CH_2)_n$ may be prepared by conventional methods, for example by reacting a salt of formula $R_1SO_2^-M^+$ (where M represents an alkali metal, such as sodium) with a compound of formula (X):

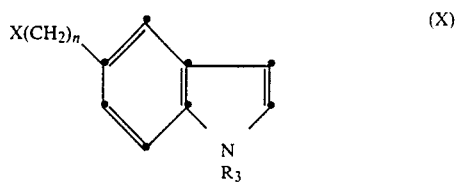

(wherein X is as previously defined and $R_3$ represents a protecting group).

The reaction may be conducted in the presence of a solvent such as an anhydrous, aprotic solvent, for example dry dimethylformamide, conveniently at room temperature.

In a particular embodiment of process (B) a compound of formula (I) is prepared by reduction of a compound of formula (VIa):

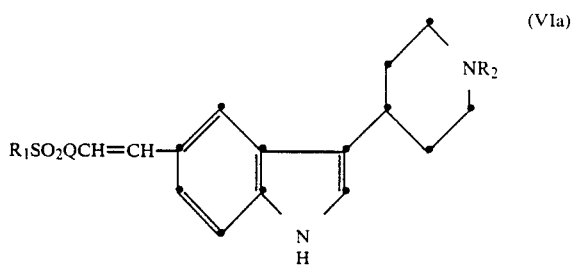

In an alternative embodiment of process (B) a compound of formula (I) is prepared by reduction of a compound of formula (VIb):

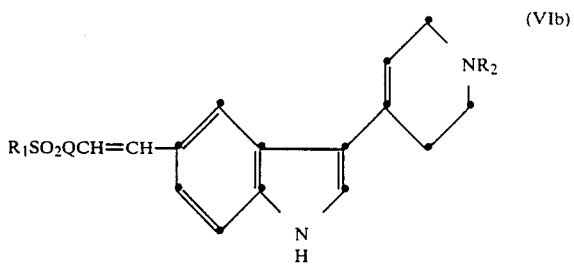

According to another general process (C) a compound of formula (I) according to the invention may be converted into another compound of the invention using conventional procedures.

According to one embodiment of general process (C), a compound of general formula (I) wherein $R_2$ represents a hydrogen atom may be alkylated using conventional techniques. The reaction may be effected using a suitable alkylating agent such as an alkyl halide, alkyl tosylate or dialkylsulphate. The alkylation reaction may conveniently be carried out in an inert organic solvent such as an amide (e.g. dimethylformamide) or an ether (e.g. tetrahydrofuran) preferably in the presence of a base. Suitable bases include, for example, alkali metal hydrides, such as sodium hydride, alkali metal carbonates, such as sodium carbonate or alkali metal alkoxides such as sodium or potassium methoxide, ethoxide or t-butoxide. The alkylation reaction is conveniently carried out at a temperature of from 25° to 100° C.

According to another general process (D), a compound of formula (I) according to the invention, or a salt thereof may be prepared by subjecting a protected derivative of formula (I) or a salt thereof to reaction to remove the protecting group or groups.

Thus, at an earlier stage in the preparation of a compound of formula (I) or a salt thereof it may have been necessary and/or desirable to protect one or more sensitive groups in the molecule to prevent undesirable side reactions.

The protecting groups used in the preparation of compounds of formula (I) may be used in conventional manner. See for example 'Protective Groups in Organic Chemistry' Ed. J. F. W. McOmie (Plenum Press 1973) or 'Protective Groups in Organic Synthesis' by Theodora W Greene (John Wiley and Sons 1981).

In compounds of formula (I) wherein $R_2$ represents hydrogen the group $NR_2$ may be protected for example by protonation or with a conventional amino protecting group. Such groups may include for example aralkyl groups, such as benzyl, diphenylmethyl or triphenylmethyl groups; and acyl groups such as N-benzyloxycarbonyl or t-butoxycarbonyl. The indole nitrogen may also be protected, for example by an aralkyl group such as benzyl.

Removal of any amino protecting groups present may be achieved by conventional procedures. Thus an aralkyl group such as benzyl, may be cleaved by hydrogenolysis in the presence of a catalyst (e.g. palladium on charcoal); an acyl group such as N-benzyloxycarbonyl may be removed by hydrolysis with, for example, hydrogen bromide in acetic acid or by reduction, for example by catalytic hydrogenation.

As will be appreciated, in some of the general processes (A) to (C) described above it may be necessary or desired to protect any sensitive groups in the molecule as just described. Thus, a reaction step involving deprotection of a protected derivative of general formula (I) or a salt thereof may be carried out subsequent to any of the above described processes (A) to (C).

Thus, according to a further aspect of the invention, the following reactions may, if necessary and/or desired be carried out in any appropriate sequence subsequent to any of the processes (A) to (C).

(i) removal of any protecting groups; and (ii) conversion of a compound of formula (I) or a salt thereof into a pharmaceutically acceptable salt or solvate (for example, hydrate) thereof.

Where it is desired to isolate a compound of the invention as a salt, for example as an acid addition salt, this may be achieved by treating the free base of general formula (I) with an appropriate acid, preferably with an equivalent amount.

As well as being employed as the last main step in the preparative sequence, the general methods indicated above for the preparation of the compounds of the invention may also be used for the introduction of the desired groups at an intermediate stage in the preparation of the required compound. It should therefore be appreciated that in such multi-stage processes, the sequence of reactions should be chosen in order that the reaction conditions do not affect groups present in the molecule which are desired in the final product.

The invention is further illustrated by the following non-limiting example. All temperatures are in ° C. Ammonia or $NH_3$ refers to 0.88 aqueous ammonia.

EXAMPLE 1

5-[2-(Ethylsulphonyl)ethyl]-3-(1-methyl-4-piperidinyl)-1H-indole hydrochloride (i) (E)-5-[2-(Ethylsulphonyl)ethenyl]-3-(1-methyl-4-piperidinyl)-1H-indole A mixture of ethyl vinyl sulphone (600 mg), 5-bromo-3-(1-methyl-4-piperidinyl)-1H-indole (1.00 g), palladium acetate (50 mg), tri-o-tolylphosphine (244 mg) and triethylamine (700 mg) in dry dimethylformamide (10 ml) was stirred and heated at 100°-110° for 4 h. The dimethylformamide and triethylamine were removed in vacuo. The residual gum was chromatographed on silica (140 g; Merck 9385), using a mixture of dichloromethane, ethanol and ammonia (80:8:1) as the eluant, to give a gum (750 mg). The material was rechromatographed on silica (Merck 9385; 100 g), using a mixture of dichloromethane, ethanol and ammonia (90:8:1) as the eluant. Fractions containing mainly the product were combined and evaporated to give a gum. A few fractions contained small amounts of the pure product. These were kept separate, combined and evaporated. The residual gum was crystallised from a small amount of a mixture of ethyl acetate and cyclohexane. Some of the crystals were then used to seed the crystallisation of the main batch of the product, also from a mixture of ethyl acetate and cyclohexane. The two batches of solid product were combined and dried in vacuo to give the title compound (310 mg) as a powder, with m.p. 98°-102°.

T.l.c. $SiO_2$ ($CH_2Cl_2$:EtOH:$NH_3$) (100:8:1). Product has Rf 0.3.

(ii) 5-[2-(Ethylsulphonyl)ethyl]-3-(1-methyl-4-piperidinyl)-1H-indole hydrochloride A solution of the product of stage (i) (280 mg) in a mixture of ethanol (40 ml), 2N hydrochloric acid (0.7 ml) and water (5 ml; added to dissolve some precipitated hydrochloride of the starting material) was hydrogenated at room temperature and atmospheric pressure, using 10% palladium on carbon (50% w/w with $H_2O$, 330 mg) as the catalyst. After 1 h; when 22 ml (0.92 mmol) of hydrogen had been absorbed, the reaction was stopped. The mixture was filtered and the filtrate was evaporated to give a foam (302 mg). The foam was crystallised from ethanol (ca. 3 ml) to give the title compound (196 mg) as a powder, with m.p. 229°-232°.

T.l.c. $SiO_2$ ($CH_2Cl_2$:EtOH:$NH_3$ 100:8:1). Product has Rf 0.25. Analysis Found: C, 56.6; H, 7.4; N, 7.2; Cl, 9.6. $C_{18}H_{26}N_2O_2S.HCl.0.45H_2O$ requires C, 57.0; H, 7.4; N, 7.4; Cl, 9.35%.

Water analysis contains 1.72% $H_2O$ w/w.

EXAMPLE 2

(3-(1-Methyl-4-piperidinyl)-5-[2-(methylsulphonyl)ethyl]-1H-indole (i) 5-Bromo-3-(1,2,3,6-tetrahydro-1-methyl-4-pyridinyl)-1H-indole, hydrochloride 1-Methyl-4-piperidone (4.0 ml) was added to a solution of 5-bromo-1H-indole (5.00 g) in methanolic potassium hydroxide (2M; 43 ml), and the stirred solution was heated at reflux for 17 h. The mixture was cooled, and the solid was filtered off affording the title free base as a white crystalline solid (7.00 g).

A sample of the base (0.61 g) was suspended in methanol (8 ml) and treated with ethereal hydrogen chloride. The resulting solution was diluted with ether (ca. 80 ml), precipitating the salt as an off-white solid (0.64 g).

Recrystallisation from 2-proponol gave the title compound.

T.l.c. (SiO$_2$ Ethyl acetate:2-proponol:water:ammonium hydroxide (50:30:16:4) Rf 0.62.

Analysis Found: C, 51.1; H, 4.9; N, 8.3; C$_{14}$H$_{15}$BrN$_2$.HCl requires C, 51.3; H, 4.9; N, 8.55%.

(ii) (E)-5-[2-(Methylsulphonyl)ethenyl]-3-(1,2,3,6-tetrahydro-1-methyl-4-pyridinyl)-1H-indole A mixture of the product of stage (i) (1.0 g), methyl vinylsulphone (0.437 g), tri-o-tolylphosphine (0.21 g), palladium acetate (0.046 g) and triethylamine (0.96 ml) in anhydrous dimethylformamide (15 ml) was stirred under nitrogen at 100° for 10 h. Methylvinylsulphone (0.218 g) was added and after another 3 h palladium acetate (0.046 g) added. Stirring at 100° was continued for another 18 h before a further portion of palladium acetate (0.046 g) was added and stirring at 100° continued for another 6 h. The dark brown suspension was evaporated to dryness and the residue purified by chromatography (Merck 9385 silica) eluting with dichloromethane:methanol:triethylamine (100:8:1)) to give the title compound as a pale green-yellow powder (0.164 g). T.l.c. (SiO$_2$ dichloromethane:ethanol:0.880 ammonia (100:8:1)) Rf 0.15

(iii) 3-(1-Methyl-4-piperidinyl)-5-[(2-methylsulphonyl)ethyl]-1H-indole

A solution of the product of stage (ii) (0.42 g) in ethanol (50 ml) and 2N hydrochloric acid (5 ml) was hydrogenated in the presence of 10% palladium oxide on carbon (1.5 g of a 50% paste in water, pre-reduced in ethanol (25 ml)). Hydrogenation was continued for ca. 18 h. The catalyst was filtered off and the solvent evaporated to give a foam. This material was purified by chromatography (Merck 9385 silica, eluant:dichloromethane/ethanol/ammonia (100/8/1)) to give a colourless gum (0.2 g). Further chromatography (Merck 9385 silica) eluting with dichloromethane:ethanol:ammonia (150:8:1)) afforded a semisolid which was triturated with anhydrous ether to give the title compound as a white powder (0.077 g) m.p. 120°-122° T.l.c. (SiO$_2$, dichloromethane:ethanol:0.88 ammonia (100:8:1); Rf 0.25.

EXAMPLE 3

3-(1-Methyl-4-piperidinyl)-5-[2-(methylsulphonyl)ethyl]-1H-indole hydrochloride

A solution of the crude product of Example 2, stage (ii) in ethanol (80 ml) containing 2N hydrochloric acid (5 ml) was hydrogenated in the presence of 10% palladium oxide on carbon (2.7 g of a 50% paste in water, pre-reduced in ethanol (30 ml)). The hydrogenation was continued for 72 h. The catalyst and solvent were removed in the normal manner and the residual brown gum crystallised from absolute alcohol to present the title compound as a fawn powder (0.42 g) m.p. 245°-250°. T.l.c. (SiO$_2$, dichloromethane:ethanol:0.880 ammonia (100:8:1)); Rf 0.2.

EXAMPLE 4

3-(1-Methyl-4-piperidinyl)-5-[(methylsulphonyl)methyl]-1H-indole (i) 4-[(Methylsulphonyl)methyl]benzeneamine A solution of 1-[(methylsulphonyl)methyl]-4-nitrobenzene (4 g) in ethyl acetate (300 ml) containing a catalytic amount of palladium on carbon (10%, prehydrogenated, 0.5 g) was hydrogenated at room temperature and pressure until hydrogen uptake ceased (1400 ml, 1 h). The catalyst was filtered off and the filter cake washed with warm ethanol (2×80 ml). The filtrates were combined and concentrated under vacuum to afford the title compound (1.9 g) as a pale yellow crystalline solid, m.p. 167°-168° C.

T.l.c. SiO$_2$, ethanol:chloroform 5:95, Rf 0.2. Assay Found: C, 51.7; H, 6.0; N, 7.4. C$_8$H$_{11}$NO$_5$S requires: C, 51.9; H, 6.0; N, 7.6%.

(ii) 4-[(Methylsulphonyl)methyl]phenylhydrazine hydrochloride

A stirred solution of the product of stage (i) (1.24 g) in dilute hydrochloric acid (5N, 20 ml) was cooled to −2° C. before a solution of sodium nitrite (0.46 g) in water (5 ml) was added dropwise over 15 min. After stirring at −2° C. for a further 15 min., a solution of stannous chloride (6 g) in concentrated hydrochloric acid (5 ml) was added in one portion to the vigorously stirred yellow solution. After 30 min at 0° C., the resulting cream suspension was allowed to come to ambient temperature over 90 min when the solid was filtered off, washed with ether (2×50 ml) and dried in vacuo overnight to afford the title compound (0.82 g) as a white solid. T.l.c. SiO$_2$, n-Butanol:water:acetic acid (4:2:1), R$_f$ 0.55.

(iii) 1-Methyl-4-piperidineacetaldehyde, 2-[4-[(methylsulphonyl)methyl]phenyl]hydrazone The product of stage (ii) (free base) (118 g) and 4-(2,2-dimethoxyethyl)-1-methylpiperidine (1.33 g) were stirred in water (100 ml) and 2N hydrochloric acid (6.5 ml) added. The mixture was stirred at room temperature for 2 h and basified with 2N aqueous sodium carbonate. The mixture was extracted with chloroform (3×100 ml), the extracts washed with brine (200 ml), dried (MgSO$_4$), filtered and evaporated to give the crude hydrazone as an orange-red oil (2.25 g). T.l.c. SiO$_2$(50:8:1 dichloromethane:ethanol:ammonia) Rf 0.40.

(iv) 5-[(Methylsulphonyl)methyl]-3-(1-methyl-4-piperidinyl)-1H-indole

The product of stage (iii) (2.25 g) was stirred in dichloromethane (100 ml) with polyphosphate ester (10 g) at reflux under nitrogen for 2 h. The mixture was poured onto ice (∼100 ml), stirred for 1 h and extracted with chloroform (3×50 ml). The extracts were washed with brine (100 m$^l$), dried (MgSO$^4$), filtered and evaporated to leave an orange foam (2.04 g). This was purified by column chromatography on silica gel (100 g Merck 7729) eluting with 75:8:1 then 50:8:1 dichloromethane:methanol:triethylamine to give the indole as a yellow oil (514 mg). This was further purified by column chromatography on silica gel (50 g Merck 7729) eluting with 50:8:1 dichloromethane:methanol:triethylamine to give the product as a white foam (453 mg).

Water assay; Found 1.01% ≡0.38 mol equiv. present. Analysis: Found: C, 57.8; H, 6.6; N, 8.1. C$_{16}$H$_{22}$N$_2$S.0.22 CHCl$_3$ 0.38 H$_2$O requires C, 57.4; H, 6.8; N, 8.25%. T.l.c. SiO$_2$ (50:8:1 dichloromethane:methanol:triethylamine Rf 0.33.

The following examples illustrate pharmaceutical formulations according to the invention containing 3-(1-methyl-4-piperidinyl)-5-[2-(methylsulphonyl)ethyl]-1H-indole as the active ingredient. Other compounds of the invention may be formulated in a similar manner.

TABLETS FOR ORAL ADMINISTRATION

A. Direct Compression

| 1. | mg/tablet |
| --- | --- |
| Active ingredient | 49 |
| Magnesium Stearate BP | 0.65 |
| Anhydrous Lactose | 81 |

The active ingredient is sieved and blended with the anhydrous lactose and magnesium stearate. The resultant mix is compressed into tablets using a Manesty F3 tablet machine fitted with 8.0 mm concave punches.

| 2. | mg/tablet |
| --- | --- |
| Active ingredient | 49 |
| Magnesium Stearate BP | 0.7 |
| Microcrystalline Cellulose NF | 91 |

The active ingredient is sieved and blended with the microcrystalline cellulose and magnesium stearate. The resultant mix is compressed into tablets using a Manesty F3 tablet machine fitted with 8.0 mm concave punches.

B. Wet Granulation

| | mg/tablet |
| --- | --- |
| Active ingredient | 7.0 |
| Lactose BP | 146.5 |
| Starch BP | 30.0 |
| Pregelatinised Maize Starch BP | 15.0 |
| Magnesium Stearate BP | 1.5 |
| Compression weight | 200.0 |

The active ingredient is sieved through a suitable sieve and blended with lactose, starch and pregelatinised maize starch. Suitable volumes of purified water are added and the powders are granulated. After drying, the granules are screened and blended with the magnesium stearate. The granules are then compressed into tablets using suitable diameter punches.

Tablets of other strengths may be prepared by altering the ratio of active ingredient to lactose or the compression weight and using punches to suit.

The tablets may be film coated with suitable film-forming materials, such as hydroxypropyl methylcellulose, using standard techniques. Alternatively the tablets may be sugar coated, or enteric coated.

| CAPSULES | mg/capsule |
| --- | --- |
| Active ingredient | 49.00 |
| *Starch 1500 | 150.00 |
| Magnesium Stearate BP | 1.00 |
| Fill Weight | 200.00 |

*A form of directly compressible starch.

The active ingredient is sieved and blended with the excipients. The mix is filled into size No. 2 hard gelatin capsules using suitable machinery. Other doses may be prepared by altering the fill weight and if necessary changing the capsule size to suit.

| SYRUP Sucrose Free Presentation | mg/5 ml dose |
| --- | --- |
| Active Ingredient | 49.00 |
| Hydroxypropylmethylcellulose USP (viscosity type 4000) | 22.5 |
| Buffer | |
| Flavour | |
| Colour | as required |
| Preservative | |
| Sweetener | |
| Purified Water BP to | 5.0 ml |

The hydroxypropylmethylcellulose is dispersed in hot water, cooled and then mixed with an aqueous solution containing the active ingredient and the other components of the formulation. The resultant solution is adjusted to volume and mixed. The syrup is clarified by filtration.

| SUSPENSION | mg/5 ml dose |
| --- | --- |
| Active ingredient | 49.00 |
| Aluminium monostearate | 75.00 |
| Sweetening agent | |
| Flavour | as required |
| Colour | |
| Fractionated coconut oil to | 5.00 ml |

The aluminium monostearate is dispersed in about 90% of the fractionated coconut oil. The resulting suspension is heated to 115° C. while stirring and then cooled. The sweetening agent, flavour and colour are added and the active ingredient is suitably dispersed. The suspension is made up to volume with the remaining fractionated coconut oil and mixed.

| SUB-LINGUAL TABLET | mg/tablet |
| --- | --- |
| Active Ingredient | 49.00 |
| Compressible Sugar NF | 50.5 |
| Magnesium Stearate BP | 0.5 |
| Compression Weight | 100.0 |

The active ingredient is sieved through a suitable sieve, blended with the excipients and compressed using suitable punches. Tablets of other strengths may be prepared by altering either the ratio of active ingredient to excipients or the compression weight and using punches to suit.

| SUPPOSITORY FOR RECTAL ADMINISTRATION | |
| --- | --- |
| Active ingredient | 49.0 mg |
| * Witepsol H15 to | 1.0 g |

* A proprietary grade of Adeps Solidus Ph. Eur.

A suspension of the active ingredient in molten Witepsol is prepared and filled, using suitable machinery, into 1 g size suppository moulds.

| INJECTION FOR INTRAVENOUS ADMINISTRATION | mg/ml |
| --- | --- |
| Active Ingredient | 0.896 |
| Sodium Chloride Intravenous Infusion, BP, 0.9% w/v to | 1 ml |
| Batch Size | 2500 ml |

The active ingredient is dissolved in a portion of the Sodium Chloride Intravenous Infusion, the solution made to volume with the Sodium Chloride Intravenous Infusion, and the solution thoroughly mixed. The solution is filled into clear, Type 1, glass 10 ml ampoules and sealed under a nitrogen headspace by fusion of the glass. The ampoules are sterilised by autoclaving at 121° C. for not less than 15 minutes.

| FOR INHALATION |  |
|---|---|
| Inhalation Cartridges |  |
|  | mg/cartridge |
| Active ingredient (micronised) | 0.56 |
| Lactose BP | 25.00 |

The active ingredient is micronised in a fluid energy mill to a fine particle size range prior to blending with normal tabletting grade lactose in a high energy mixer. The powder blend is filled into No. 3 hard gelatin capsules on a suitable encapsulating machine. The contents of the cartridges are administered using a powder inhaler such as the Glaxo Rotahaler.

| Metered Dose Pressurised Aerosol | | | |
|---|---|---|---|
| Suspension Aerosol | mg/metered dose | Per can | |
| Active ingredient (micronised) | 0.280 | 73.92 | mg |
| Oleic Acid BP | 0.020 | 5.28 | mg |
| Trichlorofluoromethane BP | 23.64 | 5.67 | g |
| Dichlorodifluoromethane BP | 61.25 | 14.70 | g |

The active ingredient is micronised in a fluid energy mill to a fine particle size range. The oleic acid is mixed with the trichloromethane at a temperature of 10°–15° C. and the micronised drug is mixed into the solution with a high shear mixer. The suspension is metered into aluminium aerosol cans and suitable metering valves, delivering 85 mg of suspension are crimped onto the cans and the dichlorodifluoromethane is pressure filled into the cans through the valves.

| Nasal Spray |  |
|---|---|
|  | % w/v |
| Active Ingredient | 7.0 |
| Preservative | as required |
| Sodium Chloride BP |  |
| Purified Water BP to | 100 |
| Shot Weight | 100 mg (equivalent to 7 mg active ingredient) |

The active ingredient, preservative and sodium chloride are dissolved in a portion of the water, the solution made to volume with the water and the solution thoroughly mixed.

The pH may be adjusted, using acid or alkali, to that of optimum stability and/or to facilitate solution of the active ingredient. Alternatively, suitable buffer salts may be used.

We claim:

1. A compound of formula (I)

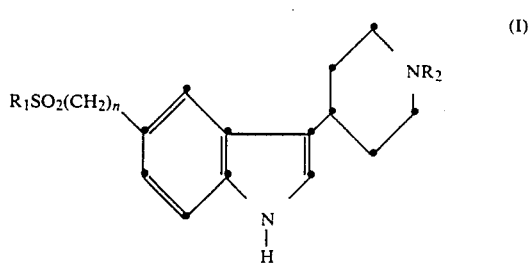

wherein
$R_1$ represents a $C_{1-6}$alkyl group;
$R_2$ represents a hydrogen atom or a $C_{1-3}$alkyl group;
n represents zero or an integer from 1 to 3;
and pharmaceutically acceptable salts thereof.

2. A compound according to claim 1 wherein $R_1$ represents a $C_{1-3}$alkyl group.

3. A compound according to claim 1 wherein $R_2$ represents a $C_{1-3}$alkyl group.

4. A compound according to claim 1 wherein $R_2$ represents a methyl group.

5. A compound according to claim 1 wherein n is 1 or 2.

6. A compound according to claim 1 wherein n is 2.

7. 5-[2-(methylsulphonyl)ethyl]-3-(1-methyl-4-piperidinyl)-1H-indole and pharmaceutically acceptable salts thereof.

8. A pharmaceutical composition which comprises an effective amount of at least one compound of formula (I) as defined in claim 1 or a pharmaceutically acceptable salt thereof together with one or more pharmaceutically acceptable carriers or excipients.

9. A pharmaceutical composition according to claim 8 adapted for oral, parenteral or intranasal administration.

10. A pharmaceutical composition according to claim 8 which is formulated in unit dosage form comprising 0.1 mg to 250 mg of a compound of formula (I) or a pharmaceutically acceptable salt thereof.

11. A method of treating a human susceptible to or suffering from migraine, cluster headache, chronic paroxysmal hemicrania or headache associated with vascular disorders which comprises administering an effective amount of a compound of formula (I) as defined in claim 1 or a pharmaceutically acceptable salt thereof.

12. A method of treating a human susceptible to or suffering from migraine, cluster headache, chronic paroxysmal hemicrania or headache associated with vascular disorders which comprises administering a pharmaceutical composition according to claim 8.

13. A method of treating a human susceptible to or suffering from migraine, cluster headache, chronic paroxysmal hemicrania or headache associated with vascular disorders which comprises administering a pharmaceutical composition according to claim 9.

* * * * *